(12) United States Patent
Friend

(10) Patent No.: US 9,519,288 B2
(45) Date of Patent: *Dec. 13, 2016

(54) OPERATOR ASSISTANCE SYSTEM

(71) Applicant: Caterpillar Inc., Peoria, IL (US)

(72) Inventor: Paul Friend, Morton, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/251,777

(22) Filed: Apr. 14, 2014

(65) Prior Publication Data

US 2014/0225755 A1 Aug. 14, 2014

Related U.S. Application Data

(63) Continuation-in-part of application No. 13/762,545, filed on Feb. 8, 2013, now Pat. No. 8,773,286.

(51) Int. Cl.
*G08G 1/017* (2006.01)
*G05D 1/02* (2006.01)
*B62D 15/02* (2006.01)

(52) U.S. Cl.
CPC .......... *G05D 1/0225* (2013.01); *B62D 15/029* (2013.01)

(58) Field of Classification Search
CPC ............. G01C 21/00; G02F 9/264; B60R 1/00
USPC ..... 340/937, 932.2, 435, 436, 438; 348/142, 348/148; 701/34.4, 36, 41
See application file for complete search history.

(56) References Cited

U.S. PATENT DOCUMENTS

| | | | |
|---|---|---|---|
| 2003/0080877 A1* | 5/2003 | Takagi et al. | 340/932.2 |
| 2004/0201671 A1* | 10/2004 | Weis et al. | 348/142 |
| 2014/0046540 A1 | 2/2014 | Ruth | |
| 2014/0261152 A1 | 9/2014 | Tanaka et al. | |

OTHER PUBLICATIONS

Paul Friend, "Truck Spotting Summary", Presentation, Automation & Enterprise Solutions, Product Development & Global Technology, Mar. 21, 2014, 24 pages, United States.
Paul Friend, "Truck Spotting Systems", Presentation, Automation & Enterprise Solutions, Product Development & Global Technology, Mar. 21, 2014, 7 pages, United States.
Elliot Duff, "Tracking a vehicle from a rotating platform with a scanning range laser", Australasian Conference on Robotics and Automation (ACRA) 2006, Dec. 6-8, 2006, Auckland, New Zealand, 7 pages, downloaded from http://www.araa.asn.au/acra/acra2006/papers/paper_5_56.pdf.

\* cited by examiner

*Primary Examiner* — Tai Nguyen
(74) *Attorney, Agent, or Firm* — L. Glenn Waterfield

(57) ABSTRACT

A system having a controller is provided. The controller receives a signal indicative of an actual position and an actual orientation of a machine on a worksite, from a position detection module. The controller determines a first view of the machine on the worksite. The first view shows the actual position of the machine and a target position of the machine. The target position is located on a bucket circle. The controller determines a second view of the machine on the worksite. The second view has a first and a second indicator. The first indicator is indicative of the actual position and the actual orientation of the machine. The second indicator is indicative of the target position and a target orientation of the machine and includes a target circle. The controller displays any one of the first view and the second view based, at least in part, on the actual position of the machine relative to the target position on a display unit.

23 Claims, 8 Drawing Sheets

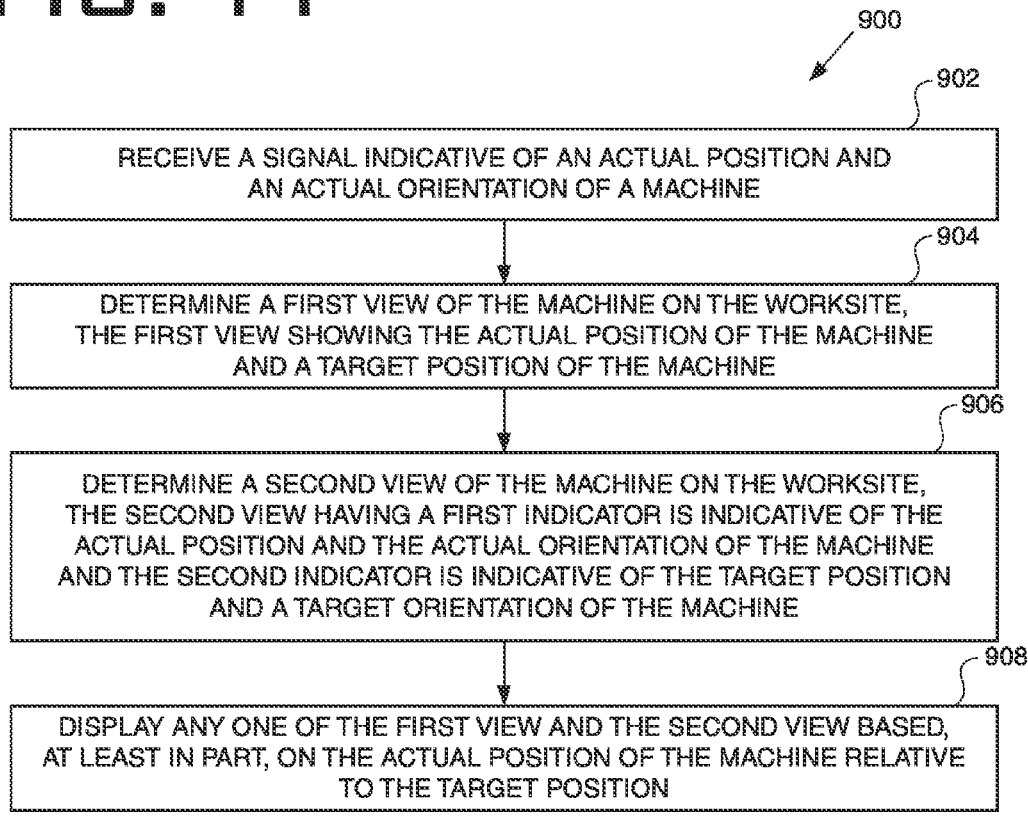

OPERATOR ASSISTANCE SYSTEM

RELATED APPLICATION

This application is a Continuation in part from U.S. application Ser. No. 13/762,545 by Paul R. Friend et al., filed Feb. 8, 2013 now U.S. Pat. No. 8,773,286.

TECHNICAL FIELD

The present disclosure relates to an operator assistance system for a machine, and more specifically to a system for assisting an operator in maneuvering the machine on a worksite.

BACKGROUND

Currently used rear parking assistance systems for vehicles include one or more rear view cameras to provide a view rearwardly of the vehicle to the operator. Additionally, proximity sensors may also be utilized in known systems to indicate the presence of nearby obstacles and/or distance of the vehicle from the obstacles. However, the known systems do not take into consideration a fixed location or target point on a site which is the final destination of the vehicle.

For example, U.S. Pat. No. 8,138,899 discloses a method for assisting a backup maneuver of a motor vehicle in which a first point of interest on the vehicle is moved toward a second point of interest remote from the vehicle. The method displays a rear contextual view on an electronic display visible to a driver of the vehicle. The rear contextual view is obtained from a rearward directed image sensor on the vehicle and includes the first point of interest and the second point of interest.

SUMMARY OF THE DISCLOSURE

In one aspect of the present disclosure, a system for assisting an operator to maneuver a machine on a worksite is provided. The system includes a position detection module configured to generate a signal indicative of an actual position and an actual orientation of the machine. The system also includes a display unit. The system further includes a controller communicably coupled to the position detection module and the display unit. The controller receives the signal indicative of the actual position and the actual orientation of the machine. The controller then determines a first view of the machine on the worksite. The first view shows the actual position of the machine and the target position of the machine, the target position being located on a bucket circle. The controller also determines a second view of the machine on the worksite. The second view has a first and a second indicator. The first indicator is indicative of the actual position and the actual orientation of the machine. The second indicator is indicative of the target position and a target orientation of the machine and includes at least a portion of a target circle. The controller then displays any one of the first view and the second view based, at least in part, on the actual position of the machine relative to the target position.

In another aspect of the present disclosure, a method for assisting an operator to maneuver a machine on a worksite is provided. The method receives a signal indicative of an actual position and an actual orientation of the machine. The method then determines a first view of to the machine on the worksite. The first view shows the actual position of the machine and the target position of the machine, the target position being located on a bucket circle. The method also determines a second view of the machine on the worksite. The second view has a first and a second indicator. The first indicator is indicative of the actual position and the actual orientation of the machine. The second indicator is indicative of the target position and a target orientation of the machine and includes at least a portion of a target circle. The method then displays any one of the first view and the second view based, at least in part, on the actual position of the machine relative to the target position.

BRIEF DESCRIPTION OF THE DRAWINGS

FIG. 11 is a flowchart of a method for assisting an operator to maneuver the machine on the worksite.

DETAILED DESCRIPTION

Figure 1:
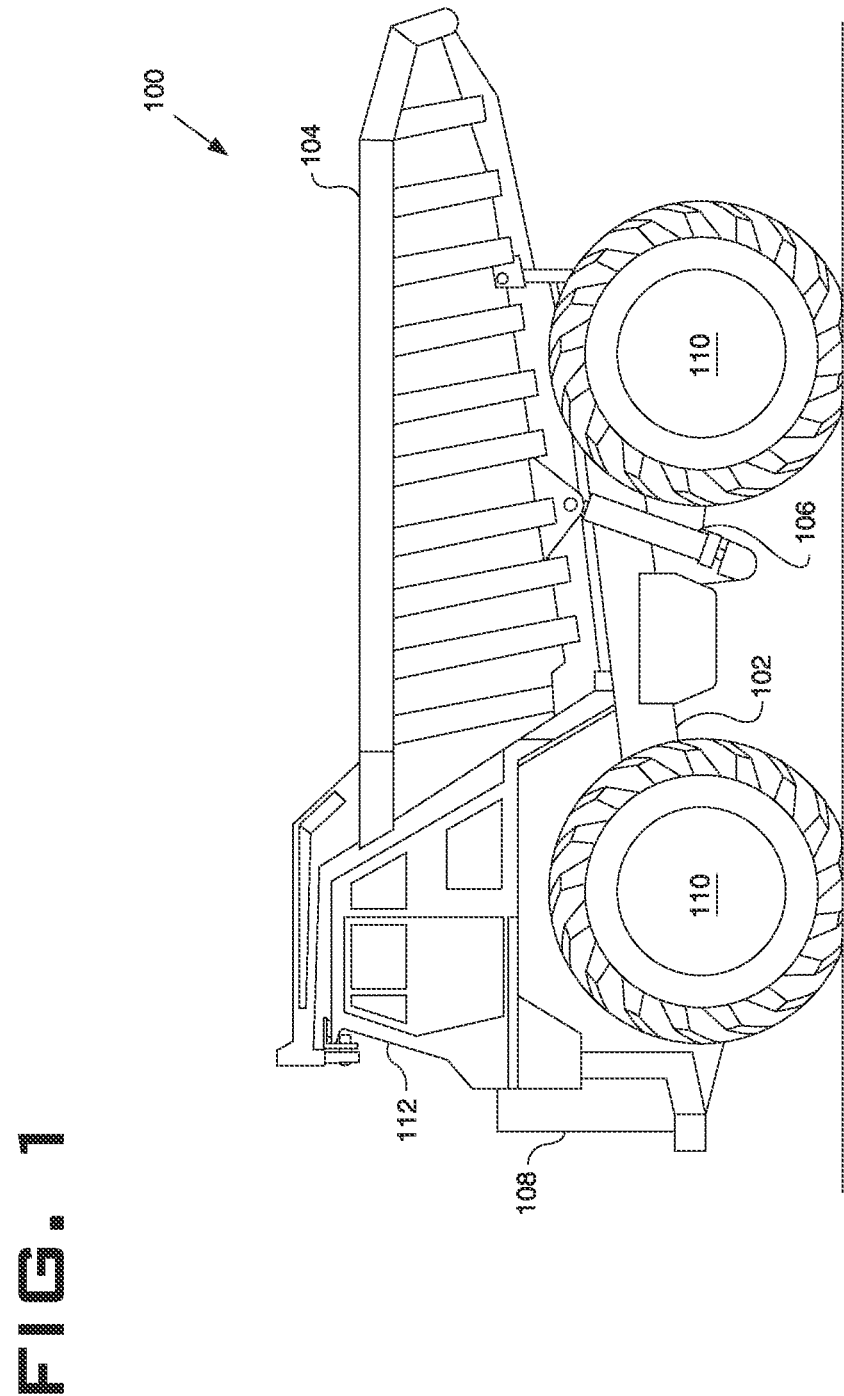
FIG. 1 is an exemplary machine, according to one embodiment of the present disclosure.

Wherever possible, the same reference numbers will be used throughout the drawings to refer to the same or the like parts. FIG. 1 illustrates an exemplary machine 100, according to one embodiment of the present disclosure. More specifically, the machine 100 is a haul truck. It should be noted that the machine 100 may include any other industrial machine including, but not limited to, a large mining truck, an articulated truck, an off-highway truck and the like. In another embodiment, the machine 100 may be one of various types of machinery used in a number of industries such as mining, agriculture, construction, forestry, waste management, and material handling, among others.

Referring to FIG. 1, the machine 100 may include a frame and/or a chassis 102. A dump body 104 may be fixedly or pivotally mounted on the chassis 102. The dump body 104 may be used for transportation of material like sand, gravel, stones, soil, excavated material, and the like from one location to another on a worksite on which the machine 100 is deployed.

Hydraulic and/or pneumatic cylinders 106 may be mounted on the chassis 102 and connected to the dump body 104 to enable movement in the form of tilting of the dump body 104 with respect to the chassis 102 of the machine 100. A powertrain or a drivetrain (not shown) may be provided on the machine 100 for the production and transmission of motive power. The powertrain may include an engine. An enclosure 108 may be provided on the chassis 102 of the machine 100 which may house the engine. The engine may be an internal combustion engine, a gas turbine, a hybrid engine, a non-conventional power source like batteries, or any other power source known in the art. A set of ground engaging members 110, like wheels, may be provided to the machine 100 for the purpose of mobility. The powertrain may further include a torque convertor, transmission inclusive of gearing, drive shafts, propeller shaft, differentials and other known drive links for transmission of motive power from the engine to the ground engaging members 110. An operator cabin 112 may be provided on the machine 100 which may house the various controls of the machine 100.

Figure 2:
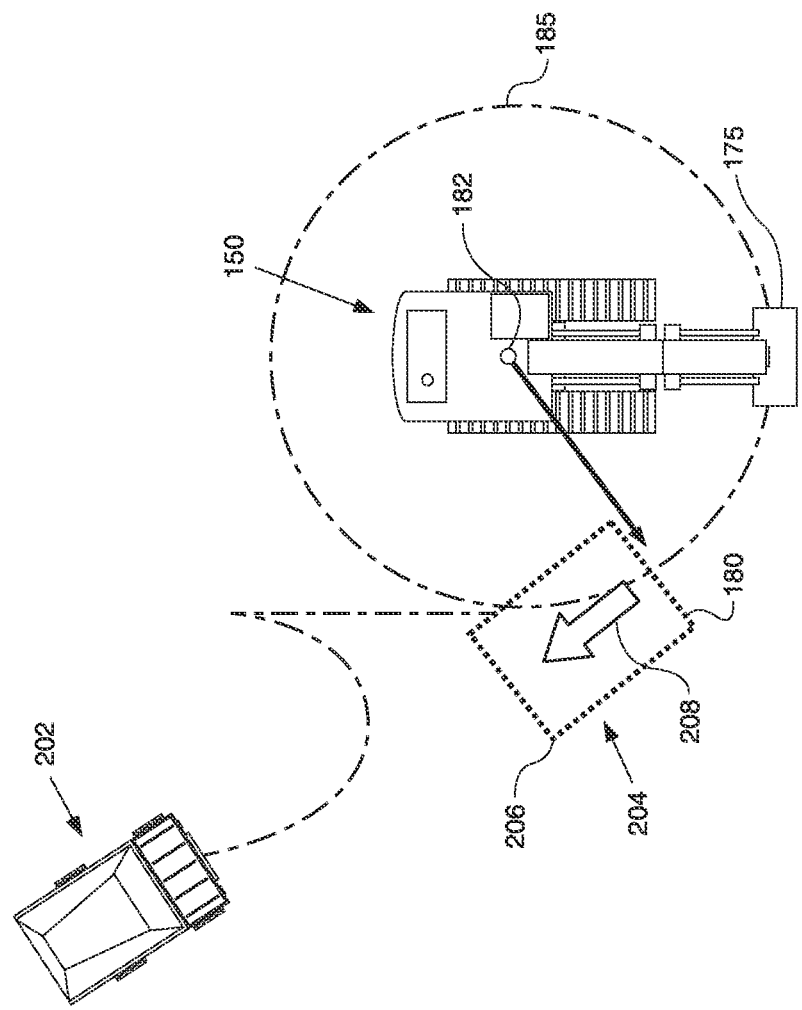
FIG. 2 is an overhead view of a worksite showing the machine and a target position and a target orientation of the machine.

The machine 100 described herein may be used for transportation of materials and/or goods from one location to another on the worksite. An exemplary worksite 200 is shown in FIG. 2. The worksite 200 may include the machine 100 at a first position 202 on the worksite 200. It may be required to maneuver the machine 100 to a second position 204 on the worksite 200. The second position 204 may include a target position 206 and a target orientation 208 of the machine 100. The target position 206 may be located on a bucket circle 185 associated with a loader 150. The target position 206 may be a fixed location on the worksite 200 which may typically include a loading or an unloading spot. Alternatively, the target position 206 may also be a parking spot, a maintenance spot, a refueling spot, etc. or any other pre-decided destination of the machine 100 on the worksite 200. The target orientation 208 may be an angular orientation and/or a directional orientation indicative of a desired direction that the machine 100 should be aligned in.

Figure 3:
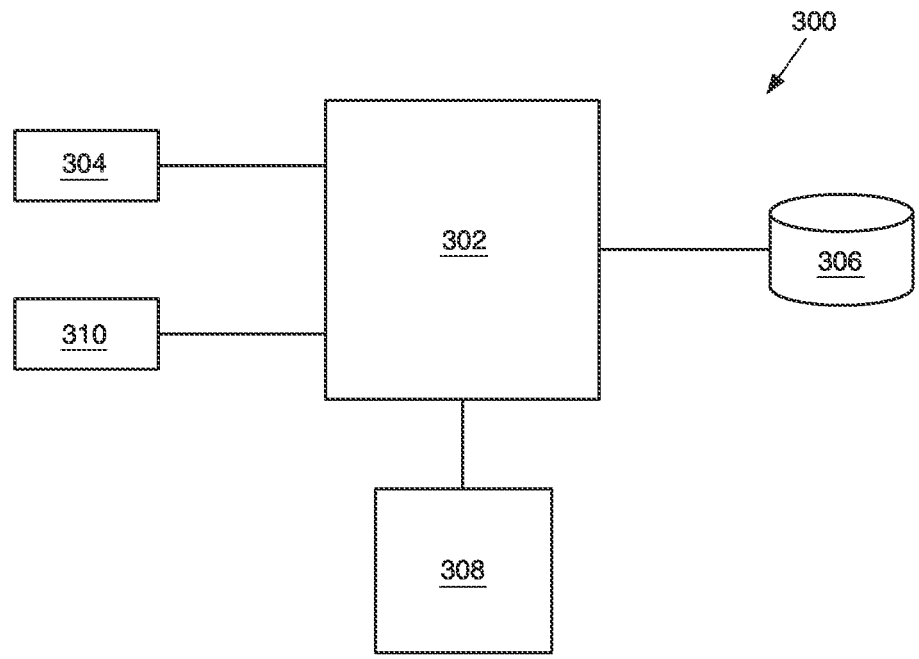
FIG. 3 is a block diagram of an operator assistance system.

Further, the machine 100 may include an operator assistance system 300, as shown in FIG. 3, which is configured to assist the operator in backing up the machine 100 to the target position 206 and in the target orientation 208 from the first position 202 on the worksite 200. Referring to FIG. 3, the operator assistance system 300 may include a controller 302 communicably coupled to a position detection module 304. The position detection module 304 may be any one or a combination of a Global Navigation Satellite System, a Global Positioning System, any other Satellite Navigation System, an Inertial Navigation System, an Augmented Navigation System or any other known positioning system. The position detection module 304 is configured to generate a signal indicative of an actual position and an actual orientation of the machine 100 on the worksite 200. The position detection module 304 is present on-board the machine 100.

As shown in FIG. 3, a database 306 may be communicably coupled to the controller 302 via a communication network (not shown). The communication network may be implemented as a wired network, a wireless network or a combination thereof. The communication network may be, but not limited to, a wide area network (WAN), a local area network (LAN), an Ethernet, Internet, an Intranet, a cellular network, a satellite network, or any other suitable network for providing communication between the database 306 and the controller 302.

Figure 7:
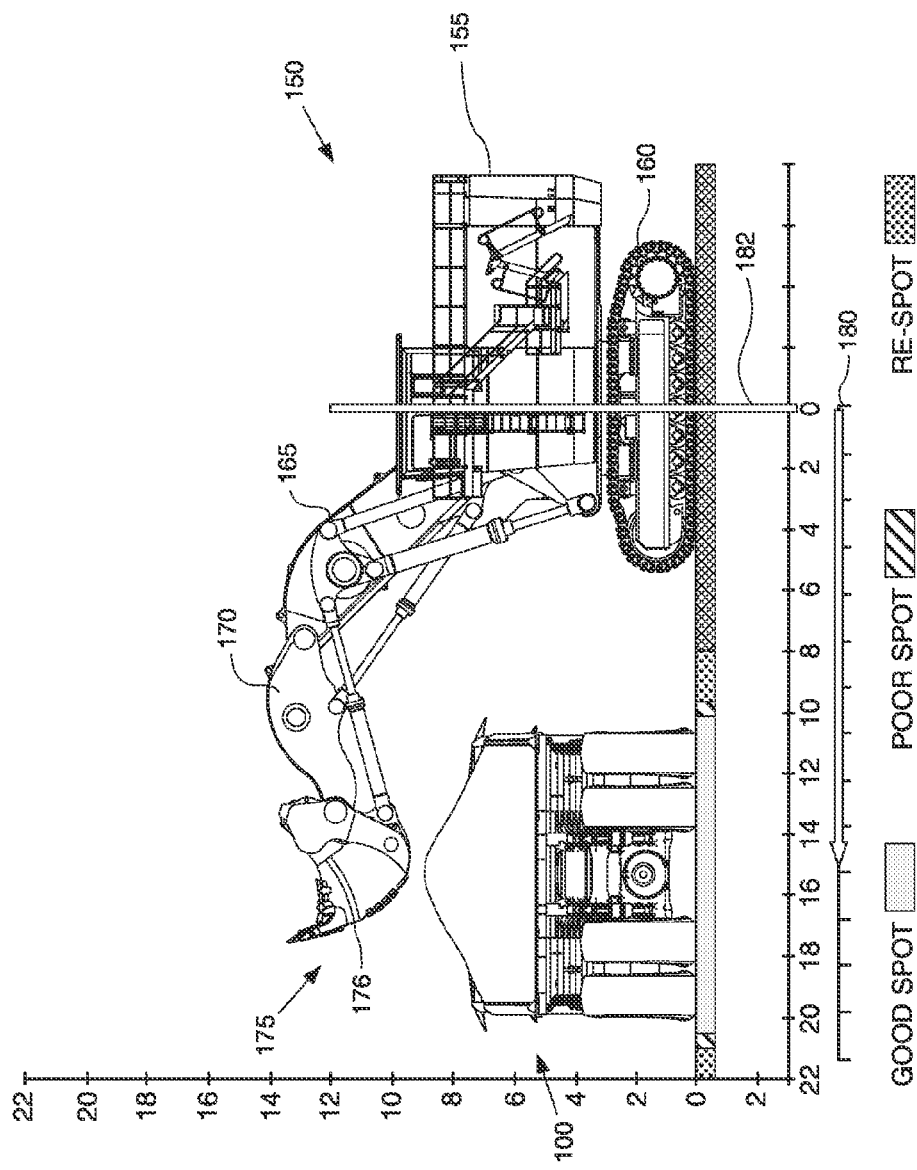
FIG. 7 is an exemplary loader shown relative to a position of a machine

As shown in FIG. 7, a loader 150 is also disclosed according to the present disclosure. The loader 150 has a rotating upper portion 155 that is mounted on a tracked lower portion 160. The upper portion 155 rotates on the lower portion 160 about a pivot axis 182. A boom 165 is hingedly attached to the upper portion 155. A bucket 175 is mounted at the end of the boom 165. In some cases, a stick 170 may be located between the boom 165 and the bucket 175. The loader 150 is configured to scoop up material into the bucket 175, lift the material by raising the boom 165, pivot to a new orientation, and then dump the material from the bucket 175. The bucket 175 may include a hinged door 176 to facilitate dumping the material. If a loader 150 is to dump the material into the back of a hauler such as machine 100, the bucket 175 must be lifted to a minimum height in order to clear the bed of machine 100.

Although bucket 175 is free to move relative to the pivot axis 182, optimal dumping is achieved when the bucket 175 is a certain distance from the pivot axis 182. This optimal dumping distance is defined as the bucket radius 180. Bucket radius 180 defines a bucket circle 185 centered on the pivot axis 182 as the upper portion 155 rotates.

Figure 4:
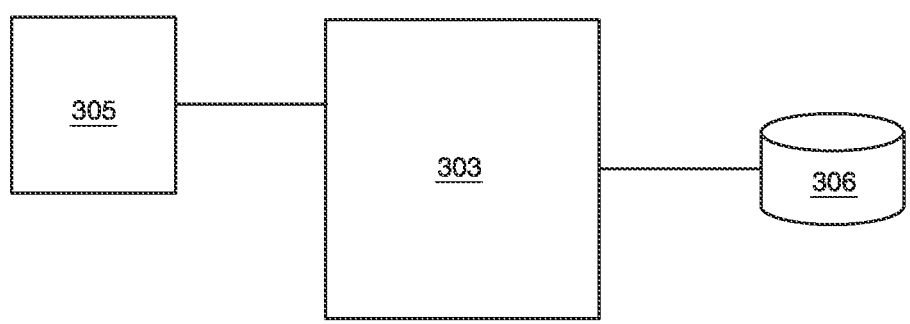
FIG. 4 is a block diagram of a controller, position detection module, and database associated with a loader

As shown in FIG. 4, loader 150 includes a controller 303 communicably coupled to a position detection module 305. The position detection module 305 may be any one or a combination of a Global Navigation Satellite System, a Global Positioning System, any other Satellite Navigation System, an Inertial Navigation System, an Augmented Navigation System or any other known positioning system. The position detection module 305 is configured to generate a signal indicative of an actual position and an actual orientation of the loader 150 on the worksite 200. The position detection module 305 is present on-board the loader 150. A database 306 may be communicably coupled to the controller 303 via a communication network (not shown). The communication network may be implemented as a wired network, a wireless network or a combination thereof. The communication network may be, but not limited to, a wide area network (WAN), a local area network (LAN), an Ethernet, Internet, an Intranet, a cellular network, a satellite network, or any other suitable network for providing communication between the database 306 and the controller 303.

The database 306 may contain data relating to the respective worksite 200 on which the machine 100 is employed. The data stored in the database 306 may include a site map, site terrain, and/or data relating to other machines employed on the worksite 200. The database 306 may therefore include the location of the loader 150, which is communicated to the database 306 from position detection module 305 through controller 303. The database 306 may also include the bucket radius 180 and therefore bucket circle 185 associated with loader 150. A person of ordinary skill in the art will realize that different sized loaders 150 will have different bucket radiuses 180. The database 306 can store a unique bucket radius 180 for each individual loader 150 or type of loader 150. Further, the database 306 may also store co-ordinates or location data related to the target position 206 of the machine 100 on the worksite 200. Additionally, the database 306 may store data related to the target orientation 208 of the machine 100 on the worksite 200. The target position 206 may be located on a bucket circle 185 and the target orientation 208 may be aligned with an imaginary line tangent to the bucket circle 185. In one embodiment, the target position 206 and the target orientation 208 may be manually fed to the operator assistance system 300. For example, the target position 206 and the target orientation 208 may be input by an operator via an operator interface device present on the machine 100. Alternatively, an on-board system of the machine 100 may determine the target position 206 and the target orientation 208 based on, for example, the position, the orientation, and physical characteristics of the machine 100. In yet another case, the on-board system on the machine 100 may be communicably connected to an off-board remote command station through a communication system present on the machine 100. In this case, the controller 302 may receive the target position and the target orientation from the remote command station.

One of ordinary skill in the art will appreciate that the database 306 may be any conventional or non-conventional database known in the art, like an oracle-based database. Moreover, the database 306 may be capable of storing and/or modifying pre-stored data as per operational and design needs. In one embodiment, the database 306 may be extrinsic to the machine 100 and located at a remote location away from the machine 100. Alternatively, the database 306 may be intrinsic to the machine 100.

The controller 302 is configured to receive the signals indicative of the actual position and the actual orientation of the machine 100 from the position detection module 304. In one embodiment, the controller 302 may retrieve the data associated with the worksite 200 from the database 306 in order to determine the actual position and the actual orientation of the machine 100 on the worksite 200, and more specifically with respect to the target position 206 and the target orientation 208 on the worksite 200.

Based on the received signal and the known sitemap of the worksite 200, the controller 302 is configured to determine a first view 400 of the machine 100 and the bucket circle 185 on the worksite 200. The first view 400 may also show the position of the loader 150. The first view 400 shows the actual position and the actual orientation of the machine 100 on the worksite 200 and the target position 206 and the target orientation 208 of the machine 100 located on the bucket circle 185 on the worksite 200. The first view 400 will be described in detail in connection with FIGS. 5 and 6. Further, the controller 302 is also configured to determine a second view 600 of the machine 100 on the worksite 200. The second view 600 is a zoomed in view of the actual position and the actual orientation of the machine 100, also showing the target position 206 and the target orientation 208 of the machine 100 located on the bucket circle 185 on the worksite 200. The second view 600 will be explained in detail in connection with FIGS. 8 to 10.

Furthermore, as shown in FIG. 3, a display unit 308 may be communicably coupled to the controller 302. Based on the actual position of the machine 100 relative to the target position 206, the controller 302 is configured to display either the first view 400 or the second view 600 of the machine 100 on to the worksite 200 on the display unit 308. For example, on reaching a predetermined distance from the target position 206, the view displayed on the display unit 308 may change from the first view 400 to the second view 600 and vice versa. Alternatively, the controller 302 may be configured to display both the first view 400 and the second view 600, simultaneously, on the display unit 308 in a split screen arrangement. The display unit 308 is preferably located in the operator cabin 112 of the machine 100. The display unit 308 may be an LCD device, an LED device, a CRT monitor, a touchscreen device or any other known display device known in the art.

Optionally, in one aspect of the current disclosure, an image capturing device 310 may be provided on the machine 100 and communicably coupled to the controller 302. The image capturing device 310 may include a CCD camera, a CMOS camera, a night vision camera or any other image capturing and/or processing device known in the art. The image capturing device 310 may be configured to provide a rearward view with respect to the machine 100. Accordingly, the controller 302 may be configured to superimpose the generated second view 600 of the machine 100 on the worksite 200 onto the feed received from the image capturing device 310, and display the same on the display unit 308.

Additionally, proximity sensors (not shown) like infrared sensors, ultrasonic sensors, laser sensors or the like may also be provided on the machine 100. The proximity sensors may be configured to determine the proximity of the machine 100 to obstacles present on the worksite 200, such as, for example, personnel working on the worksite 200, other machines, constructions like walls, pillars, etc., heaps of construction materials on the worksite 200, and the like. These signals from the proximity sensors may be sent to the controller 302.

In another aspect of the current disclosure, a steering angle sensor (not shown in figures) may be installed on the machine 100 and communicably coupled to the controller 302. The steering angle sensor may be any one or a combination of an accelerometer, a compass, a magnetometer, a gyroscope, and the like. The steering angle sensor may be configured to send signals to the controller 302 indicative of the steering angle of the machine 100, dynamic orientation and/or a direction in which the machine 100 is headed. The signal generated by the steering angle sensor, indicative of the actual orientation of the machine 100, may be sent to the controller 302. Further, the controller 302 may include data received from the steering angle sensor in the first view 400 and/or in the second view 600 of the machine 100 on the worksite 200.

Additionally, real time information like, but not limited to, actual position and co-ordinates, the target position 206 and co-ordinates, distance from the nearby obstacles, distance from the target position 206, steering angle, angle between the actual position and the target position 206 of the machine 100, preferred route of heading, deviation from the target orientation 208 and various other information may also be included in the first view 400 and/or the second view 600 and displayed on the display unit 308.

Figure 5:
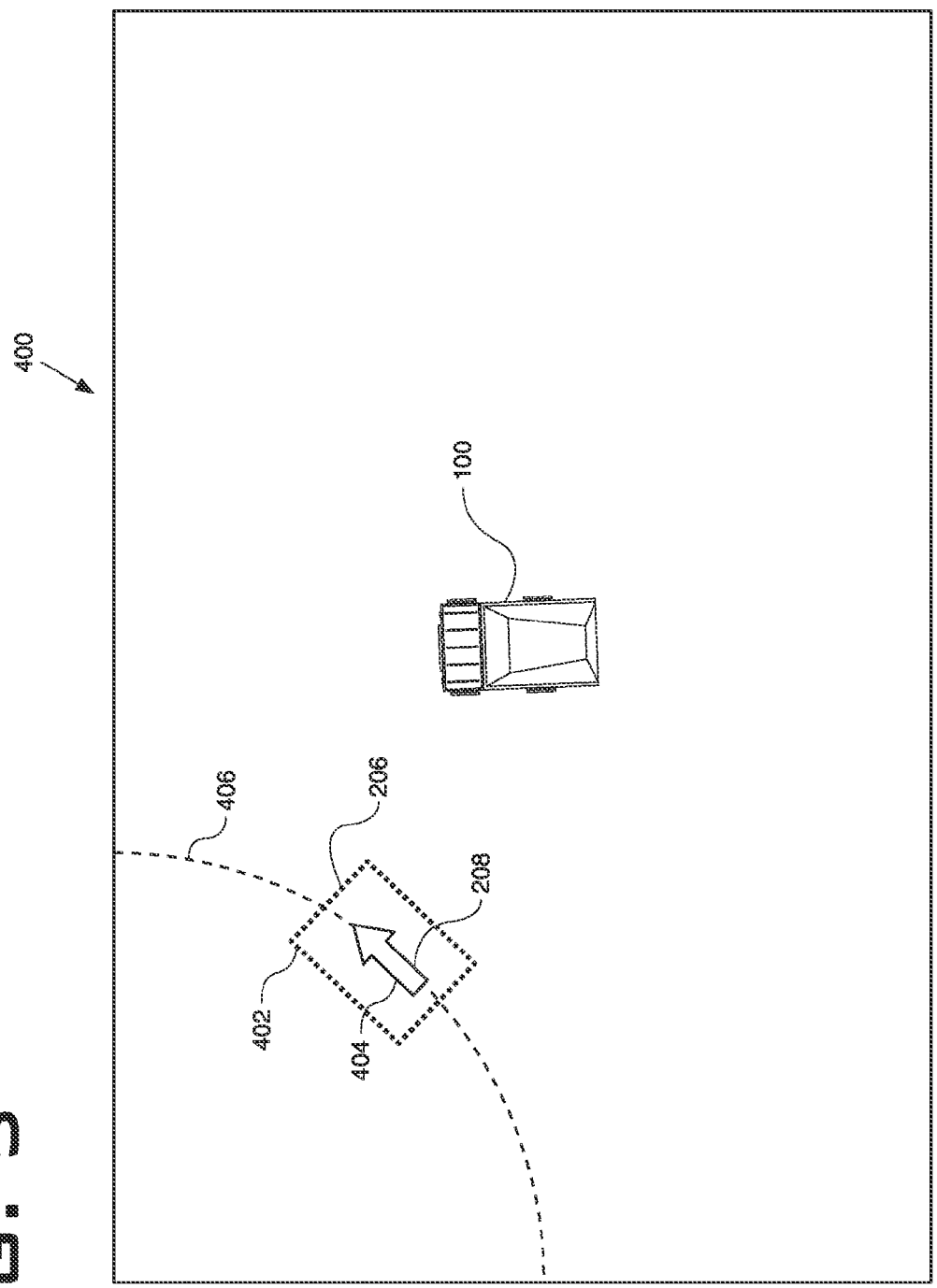
FIGS. 5 and 6 are exemplary displays of a first view of the operator assistance system.
Figure 6:
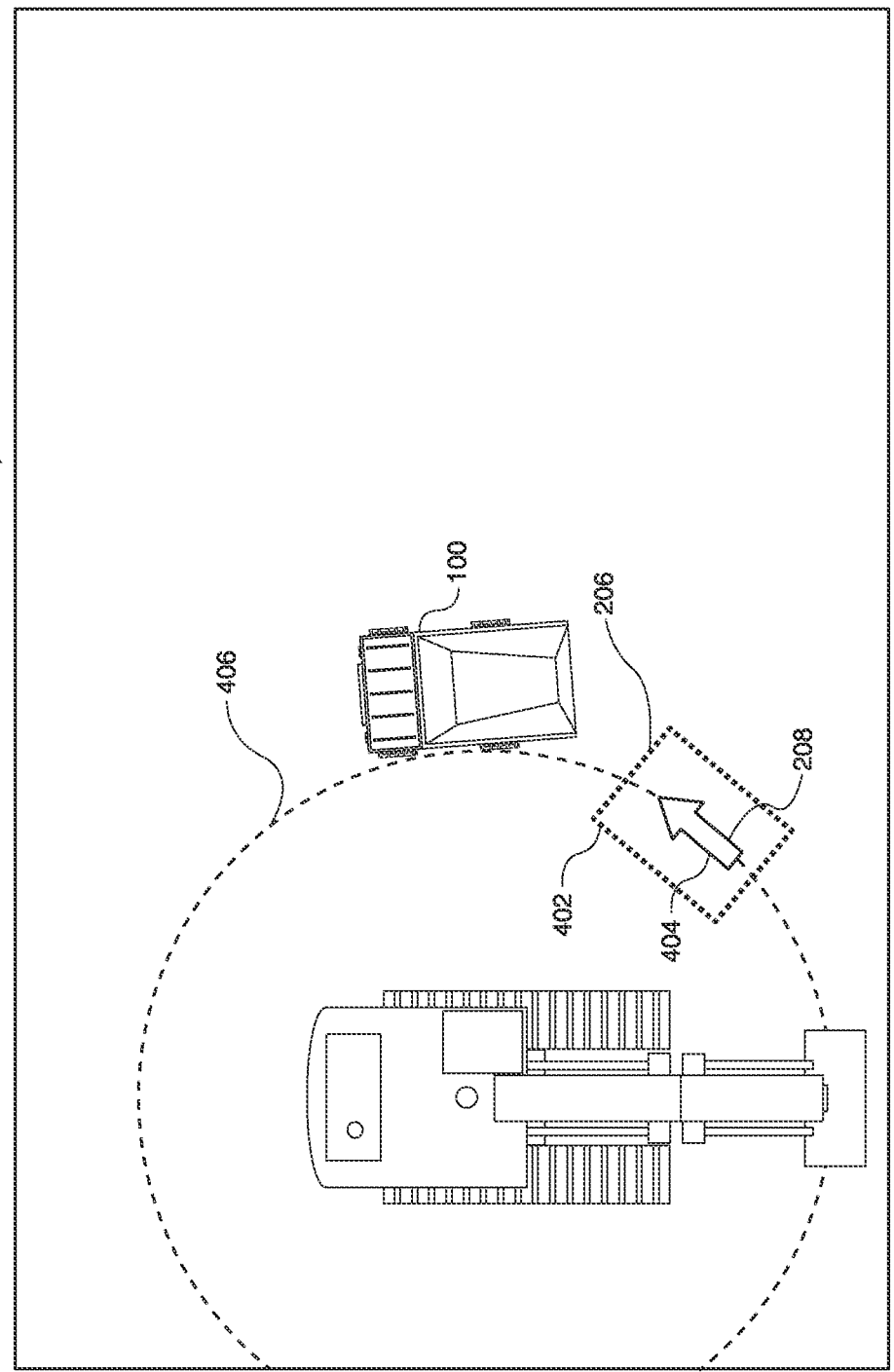

FIGS. 5, 6, and 8-10 represent exemplary displays of the operator assistance system 300. More specifically, FIGS. 5 and 6 represent first view 400 of the machine 100 on the worksite 200, which also includes the target position 206 and the target orientation 208 of the machine 100. The target position 206 of the machine 100 is depicted as a dashed box 402 in the accompanying figures. Further, the arrowhead 404 depicts the target orientation 208 of the machine 100 in the target position 206. The bucket circle 185 is depicted as target circle 406. Since the target position 206 is located on the bucket circle 185 and the target orientation 208 is aligned tangentially with the bucket circle 185, the dashed box 402 is depicted on top of the target circle 406 and the arrowhead 404 is depicted as being aligned tangentially with target circle 406.

FIGS. 5 and 6 depict different first views 400 shown to the operator on the display unit 308 as the machine 100 backs up to the target position 206 and in the target orientation 208 on the worksite 200. As shown in FIGS. 5 and 6, in this view, the actual position of the machine 100 may stay centered on the display. It should be understood that as the actual position of the machine 100 on the worksite 200 changes, the display may change such that position of the machine 100 remains centered relative to the display. Moreover, in one aspect of the current disclosure, the first view 400 may also provide information related to maneuvering the machine 100 to the target position 206 and in the target orientation 208. For example, the controller 302 may provide a suggestive path to reach the target position 206 from the actual position of the machine 100 on the worksite 200.

Figure 8:
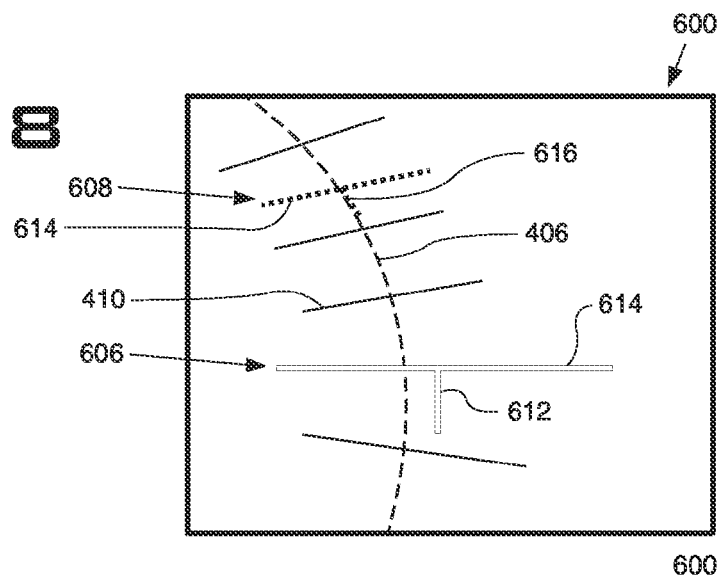
FIGS. 8 to 10 are exemplary displays of a second view of the operator assistance system.
Figure 9:
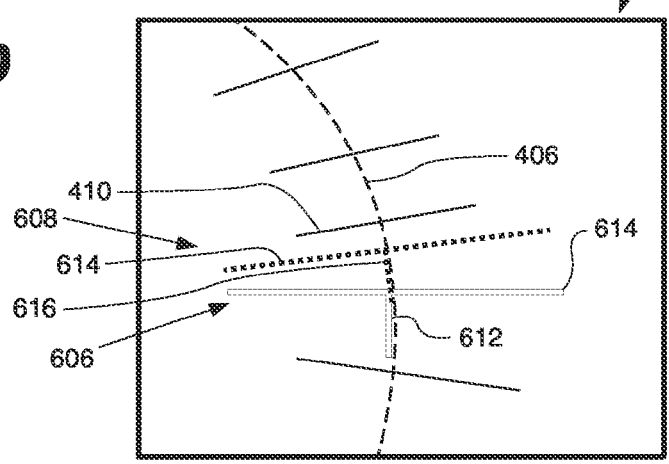
Figure 10:
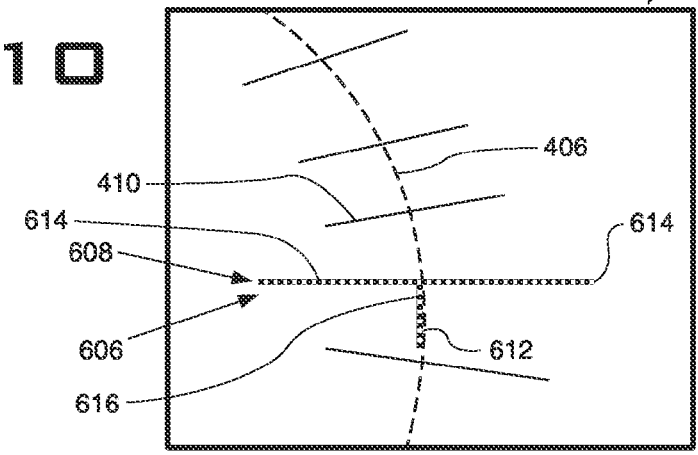

Further, based on the actual position of the machine 100 relative to the target position 206, the controller 302 may display the exemplary second view 600 relative to the machine 100, shown in FIGS. 8 to 10. For example, as the machine 100 backs up closer to the target position 206, at a predetermined distance between the actual position of the machine 100 and the target position 206, the display may change from the first view 400 to that of the second view 600. In one aspect of the current disclosure, the display may change from the first view 400 to the second view 600 on engagement of a reverse gear of the machine 100. In another aspect of the current disclosure, any combination of the distance between the actual position of the machine 100 and the target position 206, difference between the actual orientation of the machine 100 and the target orientation 208 and/or engagement of the reverse gear of the machine 100 may be utilized to change the display from the first view 400 to the second view 600. Alternatively, the operator may manually activate the change in views using controls provided in the operator cabin 112.

Referring to FIGS. 8 to 10, the second view 600 includes a linear representation of a rear end of the machine 100, and the target position 206 and the target orientation 208 on the worksite 200. FIGS. 8 to 10 depict the different second views 600 shown to the operator on the display unit 308 as the machine 100 backs up to the target position 206 and in the target orientation 208. As can be seen in the accompanying figures, the second view 600 includes a first indicator 606 and a second indicator 608. The first indicator has a "T" shaped configuration including a first line 610 and a second line 612 made of continuous lines. The first line 610 may represent the rear end of the machine 100. The second line 612 may be perpendicular to and located at the midpoint of the first line 610. The second line 612 may be indicative of the actual orientation of the machine 100. The first indicator 606 may be a fixed representation of the machine 100, based on the actual position and the actual orientation of the machine 100, relative to the worksite 200. The location of the first indicator 606 in the second view 600 may remain fixed on the display.

Similarly, a second indicator 608 configured in a "T" shape made of broken lines may be used for representing the target position 206 and the target orientation 208 of the machine 100 on the worksite 200. The second indicator 608 may include a first line 614 and a second line 616 made of broken lines. The first line 614 may represent the target position 206 of the rear end of the machine 100. The second line 616 may be perpendicular to and located at the midpoint of the first line 614. The second line 616 may be indicative of the target orientation 208 of the machine 100. The second indicator 608 further includes a target circle 406 that is representative of the bucket circle 185. The second line 616 is aligned tangentially with the target circle 406, while the first line 614 is aligned perpendicularly with the target circle 406. The second indicator 608 may further include alignment marks 410. The alignment marks 410 are depicted as line segments that are centered on and perpendicular to the target circle 406. The alignment marks 410 may be spaced regularly around the circumference of target circle 406 at a predetermined interval. The predetermined interval may vary with the distance between the machine 100 and the target position 206. The second indicator 608 may be a dynamic representation on the display, that is, the position of the second indicator 608 may change on the display as shown in FIGS. 8 to 10 depending on the actual position of the machine 100 on the worksite 200.

It should be understood that the position of the first indicator 606 is fixed whereas position of the second indicator 608 changes as seen in FIGS. 8 to 10. The second indicator 608 moves closer to the first indicator 606 and is indicative of the dynamic position of the machine 100, as the machine moves closer to the target position 206 and in the target orientation 208. When the machine 100 reaches the target position 206 and in the target orientation 208, the first indicator 606 may coincide with the second indicator 608, as shown in FIG. 10.

In one aspect of the current disclosure, the dimensions of the first indicator 606 and/or the second indicator 608 may change to indicate the proximity of the machine 100 to the target position 206. For example, as the machine 100 backs up closer to the target position 206 and in the target orientation 208, the dimensions of the second indicator 608 may increase and finally become equal to that of the first indicator 606 as shown in FIGS. 8 to 10. In another aspect of the current disclosure, the colors and representation of the first indicator 606 and the second indicator 608 may be changed as per system design and requirement. For example, the first indicator 606 and the second indicator 608 may be differentiated by the use of distinct colors. In one aspect of the current disclosure, the colors and representation of the first indicator 606 and the second indicator 608 may change to indicate the proximity of the machine 100 to the target position 206.

Additionally, the second view 600 may include distance information based on the distance between the actual position of the machine 100 on the worksite 200, and the target position 206 of the machine 100. In other words, the distance information may be a real time distance, displayed in numerical units, between the first indicator 606 and the second indicator 608. Further, the second view 600 may also include angle information based on the angle between the actual orientation of the machine 100 on the worksite 200 and the target orientation 208. In other words, the angle distance may be shown as a linear and/or a numerical representation indicative of the real time angular deviation between the actual orientation of the machine 100 and the target orientation 208.

In one aspect of the current disclosure, the controller 302 may be configured to provide assistive feedback to the operator. For example, as the machine 100 draws closer to the target position 206 and in the target orientation 208, an assistive feedback system may provide visual or audio feedback to the operator. The feedback may include information and instructions like distance left to be covered to reach the target position 206, steering angle required to reach the target orientation 208, distance from any obstacles present around the machine 100, warning signals, etc.

It should be noted that additional modifications may be made to the operator assistance system 300 and/or to the views 400, 600 represented on the display unit 308, other than the ones described herein, without departing from the intended scope of the disclosure.

INDUSTRIAL APPLICABILITY

Machines like haul trucks, mining trucks, tankers and the like need to be loaded with materials in order to transport them. For loading materials on the truck, the truck may be required to be positioned and oriented appropriately on a loading area like near a shovel, a conveyor unloading point, etc. Many a times, the truck requires to be backed up to the loading point. Proper positioning of the machine 100 beneath the bucket 175 of the loader 150, known as spotting, is essential to prevent excess spillage of material as it dumped. As is shown in FIG. 7, the operator of the machine 100 has very little margin for error when positioning the machine 100 relative to loader 150. It is particularly important that the machine 100 be spotted somewhere on the bucket circle 185. The error margin for spotting position on different points on the bucket circle 185 is lower as the operator of the loader 150 can easily make up for such spotting errors by repositioning the bucket 175 over the machine 100 with a simple swing movement. Spotting the machine 100 in a position that is not on the bucket circle 185 may require the loader 150 to relocate on the worksite 200 before dumping, which takes additional time and decreases loading efficiency. Current display systems installed on-board the machine 100 do not provide the operator with any indication of an actual position of the machine relative to the loading point.

The present disclosure provides the operator assistance system 300 which may assist in backing up the machine 100 to the target position 206 and in the target orientation 208, which the operator is made aware of by the first and second views 400, 600 shown on the display unit 308. One of ordinary skill in the art will appreciate that in addition to the machine 100 mentioned herein, the operator assistance system may also be employed on any construction, mining, agricultural, forestry or any other industrial machine and personal vehicles.

Referring to the flow chart in FIG. 11, at step 902, the controller 302 receives the signal indicative of the actual position and the actual orientation of the machine 100 on worksite 200, from the position detection module 304. The controller 302 may then retrieve data relating to the site map of the respective worksite 302, on which the machine 100 is employed, from the database 306. Based on the actual position and the actual orientation signals of the machine 100 received from the position detection module 304 and the worksite data retrieved from the database 306, the controller 302 may determine the exact current location of the machine 100 on the worksite 200.

At step 904, based on the determined actual position and the actual orientation of the machine 100 on the worksite 200 and the worksite data retrieved from the database 306, the controller 302 may determine the first view 400 to be displayed on the display unit 308. The first view 400 includes the actual position and the actual orientation of the machine 100 on the worksite 200, the target position 206, target orientation 208, and the bucket circle 185.

At step 906, the controller 302 may determine the second view 600 relative to the machine 100. The second view 600 shows the first indicator 606 and the second indicator 608. The first indicator 606 is indicative of the rear end of the machine 100. The second indicator 608 is indicative of the target position 206 and the target orientation 208 of the machine 100 located on the bucket circle 185 on the worksite 200. The dimensions, colors and representation of the first indicator 606 and the second indicator 608 may change based on the distance of the machine 100 from the target position 206. In one aspect of the current disclosure, the controller 302 may impose the second view 600 on the images captured by the image capturing device 310. This may provide a better detailing in the second view 600 with the inclusion of real time images of the worksite 200.

At step 908, any one of the first view 400 and the second view 600 is displayed on the display unit 308. The display may change from the first view 400 to the second view 600 based on the proximity of the machine 100 to the target position 206 on the worksite 200. Alternatively, the display may change from the first view 400 to the second view 600 based on difference between the actual orientation of the machine 100 and the target orientation 208, engagement of the reverse gear of the machine 100 and/or voluntarily by the operator using additional controls on the operator assistance system 300.

In addition, the controller 302 may also be configured to display additional information including actual position of the machine 100 and its co-ordinates, target position 206 and its co-ordinates, distance from the nearby obstacles, distance from the target position 206, steering angle, angle between the actual orientation of the machine 100 and the target orientation 208, preferred route of heading and the like in the first view 400 and/or the second view 600.

While aspects of the present disclosure have been particularly shown and described with reference to the aspects of the current disclosure above, it will be understood by those skilled in the art that various additional aspects of the current disclosure may be contemplated by the modification of the disclosed machines, systems and methods without departing from the spirit and scope of what is disclosed. Such aspects of the current disclosure should be understood to fall within the scope of the present disclosure as determined based upon the claims and any equivalents thereof.

What is claimed is:

1. A system for assisting an operator to maneuver a machine on a worksite, the system comprising:
   a position detection module configured to generate a signal indicative of an actual position and an actual orientation of the machine;
   a display unit; and
   a controller communicably coupled to the position detection module and the display unit, the controller configured to:
      receive the signal, indicative of the actual position and the actual orientation of the machine;
      determine a first view of the machine on the worksite, the first view showing the actual position of the machine and a target position of the machine, the target position being located on a bucket circle;
      determine a second view of the machine on the worksite, the second view having a first and a second indicator, wherein the first indicator is indicative of the actual position and the actual orientation of the machine and the second indicator is indicative of the target position and a target orientation of the machine and includes at least a portion of a target circle; and
      display any one of the first view and the second view based, at least in part, on the actual position of the machine relative to the target position.

2. The system of claim 1 further comprising an image capturing device communicably coupled to the controller, the image capturing device configured to capture a view rearwardly of the machine.

3. The system of claim 2, wherein the controller is further configured to receive, from the image capturing device, the view captured rearwardly of the machine.

4. The system of claim 3, wherein the controller is configured to display the determined second view imposed on the view captured rearwardly of the machine.

5. The system of claim 1 further comprising a steering angle sensor configured to generate a signal indicative of a steering angle of the machine.

6. The system of claim 5, wherein the controller is further configured to determine the actual orientation of the machine based on the steering angle of the machine.

7. The system of claim 1, wherein the second view further comprises distance information based on a distance between the actual position of the machine and the target position of the machine.

8. The system of claim 1, wherein the second view further comprises angle information based on an angle between the actual orientation of the machine and the target orientation of the machine.

9. The system of claim 1, wherein a color of any one of the first indicator and the second indicator is based on a distance between the actual position of the machine and the target position of the machine.

10. The system of claim 1, wherein the first indicator includes a fixed representation based on the actual position and the actual orientation of the machine.

11. The system of claim 1, wherein the second indicator includes a dynamic representation based on the target position and the target orientation of the machine.

12. The system of claim 1, wherein the first indicator and the second indicator include a "T" shaped configuration.

13. The system of claim 1 wherein the second indicator further comprises alignment marks centered on and perpendicular to the target circle.

14. A method for assisting an operator to maneuver a machine on a worksite, the method comprising:
receiving a signal indicative of an actual position and an actual orientation of the machine;
determining a first view of the machine on the worksite, the first view showing the actual position of the machine and a target position of the machine, the target position being located on a bucket circle;
determining a second view of the machine on the worksite, the second view having a first and a second indicator, wherein the first indicator is indicative of the actual position and the actual orientation of the machine and the second indicator is indicative of the target position and a target orientation of the machine and includes at least a portion of a target circle; and
displaying any one of the first view and the second view based, at least in part, on the actual position of the machine relative to the target position.

15. The method of claim 14 further comprising receiving a view captured rearwardly of the machine.

16. The method of claim 14 further comprising displaying the determined second view imposed on the view captured rearwardly of the machine.

17. The method of claim 14 further comprising displaying distance information in the second view, the distance information based on a distance between the actual position of the machine and the target position of the machine.

18. The method of claim 14 further comprising displaying angle information in the second view, the angle information based on an angle between the actual orientation of the machine and the target orientation of the machine.

19. The method of claim 14 wherein the second indicator further comprises alignment marks centered on and perpendicular to the target circle.

20. A machine operating on a worksite, the machine comprising:
a power source;
a frame;
a position detection module configured to generate a signal indicative of an actual position and an actual orientation of the machine;
a display unit; and
a controller communicably coupled to the position detection module and the display unit, the controller configured to:
receive the signal indicative of the actual position and the actual orientation of the machine;
determine a first view of the machine on the worksite, the first view showing the actual position of the machine and a target position of the machine, the target position being located on a bucket circle;
determine a second view of the machine on the worksite, the second view having a first and a second indicator, wherein the first indicator is indicative of the actual position and the actual orientation of the machine and the second indicator is indicative of the target position and a target orientation of the machine and includes at least a portion of a target circle; and
display any one of the first view and the second view based, at least in part, on the actual position of the machine relative to the target position.

21. The machine of claim 20 further comprising an image capturing device communicably coupled to the controller, the image capturing device configured to capture a view rearwardly of the machine.

22. The machine of claim 20, wherein the controller is configured to display the determined second view imposed on the view captured rearwardly of the machine.

23. The machine of claim 20 wherein the second indicator further comprises alignment marks centered on and perpendicular to the target circle.

* * * * *